United States Patent
Lindqvist et al.

(10) Patent No.: US 11,638,701 B2
(45) Date of Patent: May 2, 2023

(54) FORMULATION OF GAMMA-AMINOBUTYRIC ACID

(71) Applicant: DIAMYD MEDICAL AB, Stockholm (SE)

(72) Inventors: Anton Lindqvist, Stockholm (SE); Ulf Hannelius, Stockholm (SE)

(73) Assignee: DIAMYD MEDICAL AB, Stockholm (SE)

( * ) Notice: Subject to any disclaimer, the term of this patent is extended or adjusted under 35 U.S.C. 154(b) by 166 days.

(21) Appl. No.: 16/644,938

(22) PCT Filed: Aug. 24, 2018

(86) PCT No.: PCT/SE2018/050855
§ 371 (c)(1),
(2) Date: Mar. 5, 2020

(87) PCT Pub. No.: WO2019/059822
PCT Pub. Date: Mar. 28, 2019

(65) Prior Publication Data
US 2021/0137867 A1    May 13, 2021

(30) Foreign Application Priority Data

Sep. 19, 2017   (SE) .................................... 1751159-3

(51) Int. Cl.
| | |
|---|---|
| *A61K 31/197* | (2006.01) |
| *A61P 3/10* | (2006.01) |
| *A61K 9/00* | (2006.01) |
| *A61K 47/02* | (2006.01) |
| *A61K 47/38* | (2006.01) |

(52) U.S. Cl.
CPC .......... *A61K 31/197* (2013.01); *A61K 9/0053* (2013.01); *A61K 47/02* (2013.01); *A61K 47/38* (2013.01); *A61P 3/10* (2018.01)

(58) Field of Classification Search
CPC .... A61K 31/197; A61K 9/0053; A61K 47/02; A61K 47/38
See application file for complete search history.

(56) References Cited

U.S. PATENT DOCUMENTS

2005/0226927 A1   10/2005   Han et al.
2014/0322213 A1   10/2014   Wang et al.

FOREIGN PATENT DOCUMENTS

| CN | 103054044 | * | 4/2013 |
|---|---|---|---|
| CN | 103054044 A | | 4/2013 |

(Continued)

OTHER PUBLICATIONS

English translation of CN 103054044 (Year: 2013).*
(Continued)

*Primary Examiner* — San Ming R Hui
(74) *Attorney, Agent, or Firm* — James S. Keddie; Bozicevic, Field & Francis LLP (57) ABSTRACT

The present invention relates to an oral dosage form comprising gamma-aminobutyric acid (GABA) and pharmaceutically acceptable excipients, wherein 100% of the GABA is released within 0.25-5 hours in 0.01 M HCl at 37° C. in a USP dissolution apparatus 2. The invention further relates to specific dosage forms, methods for treatment of autoimmune diseases with the dosage form, as well as use of the dosage form in such methods.

15 Claims, 6 Drawing Sheets

(56) References Cited

FOREIGN PATENT DOCUMENTS

| | | | |
|---|---|---|---|
| CN | 106606495 | A | 5/2017 |
| EP | 3645014 | A1 | 5/2020 |
| JP | 2003088335 | A | 3/2003 |
| JP | 2008074734 | A | 4/2008 |
| JP | 2010189333 | A | 9/2010 |

OTHER PUBLICATIONS

Maroni et al., Journal of Pharmaceutical Sciences, 2007;96(6):1527-1536 (Year: 2007).*
Product information of Dicalcium phosphate, anhydrous, Innophos, Jun. 19, 2006. (Year: 2006).*
AOV 1142 GABA Supplement. Datasheet [online]. AOV, May 2013, Record ID 2082289, retrieved from <http://www.gnpd.com>.
Anonymous: "GABA (gamma aminobutyric acid) supplements with the fewest additives—Toxinless", Toxinless.com, 2014, pp. 1-5, retrieved from the Internet: URL:https://www.toxinless.com/gaba.
Database GNPD [Online] MINTEL, anonymous: "GABA Food Supplement Powder", XP055799639, Database accession No. 4543403, 2017.
Anonymous: "PharmaGABA-250—Contains natural-source GABA, a brain chemical to promote a calm state of mind and restful sleep* | Thorne", Thorne Research, 2015, retrieved from the Internet: URL:https://www.thorne.com/products/dp/pharmagaba-250, p. 1/1.

\* cited by examiner

FORMULATION OF GAMMA-AMINOBUTYRIC ACID

CROSS-REFERENCE TO RELATED APPLICATIONS

This application is a § 371 national phase of International Application No. PCT/SE2018/050855, filed on Aug. 24, 2018, which claims the benefit of Swedish Application No. 1751159-3, filed on Sep. 19, 2017, which applications are incorporated by reference herein.

FIELD OF THE INVENTION

The present invention relates to the field of medicine and pharmaceutical formulations. In particular, it relates to pharmaceutical formulations comprising gamma-aminobutyric acid and their use in treatment of metabolic disorders.

BACKGROUND

Gamma-aminobutyric acid (GABA) also known as 4-aminobutanoic acid, CAS registry no. 56-12-2, is a naturally occurring neurotransmitter with central nervous system (CNS) inhibitory activity. GABA is commercially available as a food supplement, but is regulated as a pharmaceutical substance in some countries. In the ATC classification system, it is classified as an antiepileptic with a defined daily dose of 1 g via oral or parenteral administration. GABA is also produced in islets cells where it regulates hormone secretion of pancreatic cells through $GABA_A$-receptors.

GABA has been suggested for use in therapeutic or prophylactic amelioration of symptoms and disorders associated with metabolic syndrome, such as type 1 diabetes, cf. WO2012/050907. It is suggested that a sustained release oral dosage form that releases the drug from the dosage form over a period of at least 6 hours is used for this therapeutic or prophylactic treatment.

Li and co-workers (Li et al., Frontiers in Pharmacology, (2015) 6:260) studied pharmacokinetics and pharmacodynamics of GABA in healthy volunteers. GABA was administered in doses of 2 g once or three times per day in a fasting state. The type of pharmaceutical formulation used is not specified. No data relating to administration with meals are shown.

SUMMARY OF THE INVENTION

It is the object of the present invention to provide improved formulations of gamma-aminobutyric acid, in particular for use in treatment or prevention of diabetes and/or metabolic syndrome. Specifically, the formulation provides comparable bioavailability of GABA irrespective of accompanying meals.

In one aspect, the present invention relates to an oral dosage form comprising gamma-aminobutyric acid (GABA) and pharmaceutically acceptable excipients, wherein 100% of the GABA is released within 0.25-5 hours in 0.01 M HCl at 37° C. in a USP dissolution apparatus 2.

In a further aspect, the present invention relates to an oral dosage form comprising gamma-aminobutyric acid (GABA), wherein the dosage form comprises 30-50% GABA, 1-35% hydroxypropyl methylcellulose, and pharmaceutically acceptable excipients.

In a further aspect, the present invention relates to an oral dosage form comprising gamma-aminobutyric acid (GABA) and pharmaceutically acceptable excipients, wherein the dosage form exhibits a AUC (5 h) when administered to a patient in fed state that is +/−30% as compared to AUC (5 h) when administered to a patient in fasting state.

In a further aspect, the present invention relates to an oral dosage form according to the invention for use in a method for treatment or prevention of diabetes or metabolic syndrome in a subject.

In a further aspect, the present invention relates to the use of GABA in a method for producing an oral dosage form according to the invention for use in a method for treatment or prevention of diabetes or metabolic syndrome in a subject.

In a further aspect, the present invention relates to a method for treatment or prevention of diabetes or metabolic syndrome in a subject comprising administering an oral dosage form according to the invention to said subject.

Preferred embodiments of the invention are set out in the dependent claims.

DEFINITIONS

AUC (x h): The area under the drug plasma concentration curve from time of administration to x hours. That is AUC (5 h) is the area under the drug plasma concentration curve from time of administration to 5 hours.

Cmax: The maximum drug plasma concentration obtained after administration of the drug.

Tmax: The time at which the maximum drug plasma concentration is obtained after administration of the drug.

All percentages in relation to compositions are given as weight/weight (w/w) percentages, unless otherwise stated.

DETAILED DESCRIPTION

The present inventors have realized that uptake of orally administered GABA is significantly influenced by the formulation used and also depends on food intake of the patient taking GABA. It is preferable to have a formulation that can be taken both with and without food and that provides comparable bioavailability of GABA irrespective of accompanying meals.

This is even more preferable in therapy regimens that continue for a significant period of time, such as months or years, as detailed administration requirements, such as the need to take the drug with meals or in a fasting state, tend to decrease adherence to the prescribed regimen and may result in a loss of therapeutic effect.

The present inventors have also realized that GABA is only taken up by a patient during the first 2-3 hours after oral administration.

The invention thus relates to an oral dosage form comprising gamma-aminobutyric acid (GABA) and pharmaceutically acceptable excipients, having comparable bioavailability in terms of AUC, when administered to a patient in fed and fasting state, respectively.

In one embodiment, comparable bioavailability in terms of AUC is defined as that the dosage form exhibits an AUC (5 h) when administered to a patient in fed state that is within +/−30% as compared to AUC (5 h) when administered to a patient in fasting state, using a dose of 20 mg/kg.

The comparable bioavailability in terms of AUC, of a dosage form according to the invention may be achieved with an oral dosage form wherein 100% of the GABA is released within 0.25-5 hours in 0.01 M HCl at 37° C. in an USP dissolution apparatus 2. Thus, in one aspect, the invention relates to an oral dosage form comprising gamma-aminobutyric acid (GABA) and pharmaceutically acceptable excipients, wherein 100% of the GABA is released within 0.25-5 hours in 0.01 M HCl at 37° C. in a USP dissolution apparatus 2.

In one embodiment, at least 95% of the GABA is released after 4 hours in 0.01 M HCl at 37° C. in an USP dissolution apparatus 2.

In one embodiment, at least 95% of the GABA is released after 3 hours in 0.01 M HCl at 37° C. in an USP dissolution apparatus 2.

In one embodiment, at least 95% of the GABA is released after 1 hour in 0.01 M HCl at 37° C. in an USP dissolution apparatus 2.

The release of GABA may be measured in an USP dissolution apparatus 2 in 1000 ml of 0.01M HCl where the oral dosage forms are mixed using a paddle speed of 50 rpm at 37° C.

That 100% of the GABA is released within a specified time span shall be construed to mean that less than 100% of the GABA has been released prior to the specified time span.

The USP dissolution apparatus 2 is an apparatus for determining dissolution characteristics for oral dosage forms. Both the apparatus and the methods for using the apparatus are standardized and harmonized across the United States, European, and Japanese pharmacopoeias, and extensively described in chapter <711> Dissolution, incorporated herein by reference.

The comparable bioavailability in terms of AUC of a dosage form according to the invention may also be achieved with an oral dosage form wherein the dosage form comprise 30-50% GABA, 50-60% filler material, and optionally pharmaceutically acceptable excipients. Thus, in one aspect, the invention relates to a dosage form that comprises 30-50% GABA, 50-60% filler material, and optionally pharmaceutically acceptable excipients.

Filler materials are well-known in the art and include cellulose (such as microcrystalline cellulose, cellulose ethers, plant based cellulose), starch, dicalcium phosphate.

Hydroxypropylmethylcellulose ethers useful as fillers are commercially available under the trade name Methocel™ (Dow Chemical Company).

In one embodiment, the dosage form according to the invention comprises 30-35% hydroxypropyl methylcellulose.

In one embodiment the hydroxypropyl methylcellulose has a methoxyl substitution grade of 28-30% as a filler material.

In one embodiment, the hydroxypropyl methylcellulose has viscosity of 80-120 mPa at 2% in water at 20° C.

In one embodiment the hydroxypropyl methylcellulose has a viscosity of 40-60 mPa·s at 2% in water and 20° C.

In one embodiment the hydroxypropyl methylcellulose has a viscosity of 2.5-5.0 mPa·s at 2% in water and 20° C.

In one embodiment, the hydroxypropyl methylcellulose has a methoxyl substitution grade of 19-24%.

In one embodiment, the hydroxypropyl methylcellulose has a methoxyl substitution grade of 28-30%.

In one embodiment, the dosage form according to the invention comprises 40% GABA, 30-35% hydroxypropyl-methylcellulose with a methoxyl substitution grade of 28-30% and a viscosity of 40-60 mPa·s at 2% in water at 20° C., 23.5-28.5% microcrystalline cellulose, and optionally further pharmaceutically acceptable excipients.

In one embodiment, the dosage form according to the invention comprises 40% GABA, 30% hydroxypropyl methylcellulose with a methoxyl substitution grade of 28-30% and a viscosity of 2.5-5.0 mPa at 2% in water at 20° C., 28.5% microcrystalline cellulose, and optionally further pharmaceutically acceptable excipients.

In one embodiment, the dosage form according to the invention comprises 40% GABA, 30% hydroxypropyl methylcellulose with a methoxyl substitution grade of 19-24% and a viscosity of 80-120 mPa at 2% in water at 20° C., 28.5% microcrystalline cellulose, and optionally further pharmaceutically acceptable excipients.

In one embodiment of the invention, the filler materials comprises microcrystalline cellulose and/or dicalcium phosphate.

In one embodiment, the dosage form further comprises a disintegrant, and optionally further pharmaceutically acceptable excipients.

In one embodiment, the oral dosage form comprises 30-40% microcrystalline cellulose, and 15-20% dicalcium phosphate.

In one embodiment, the oral dosage form comprises 40% GABA, 36.75% microcrystalline cellulose, and 16.75% dicalcium phosphate, a disintegrant (such as croscarmellose sodium), and optionally further pharmaceutically acceptable excipients.

In one embodiment, at least 95% of the GABA is released after 4 hours in 0.01 M HCl at 37° C. in an USP dissolution apparatus 2.

In one embodiment, at least 95% of the GABA is released after 3 hours in 0.01 M HCl at 37° C. in an USP dissolution apparatus 2.

In one embodiment, at least 95% of the GABA is released after 1 hour in 0.01 M HCl at 37° C. in an USP dissolution apparatus 2.

In one aspect of the invention, the oral dosage form comprises 40% GABA.

In one aspect of the invention, the oral dosage form comprises 200 mg GABA.

The pharmaceutically acceptable excipients may include glidant, lubricants, colouring agents, flavouring agents, coating agents, taste masking agents, disintegrants etc. as known in the art.

These include cellulose, microcrystalline cellulose, silicon dioxide, magnesium stearate, calcium stearate, croscarmellose sodium etc.

The oral dosage form may be a solid oral dosage form, such as a tablet, capsule or the like.

In a further aspect, the invention relates to an oral dosage form according to the invention for use in a method of treatment or prevention of diabetes or metabolic syndrome. Diabetes includes type 1 diabetes, type 2 diabetes, gestational diabetes, and latent autoimmune diabetes in adults (LADA). Metabolic syndrome is a cluster of metabolic risk factors for cardiovascular disease and type 2 diabetes, comprising excess abdominal fat; atherogenic dyslipidemia;

hypertension; hyperglycemia; insulin resistance; a proinflammatory state; and a prothrombotic state.

In a further aspect, the invention relates to the use of GABA in a method for the manufacture of an oral dosage form according to the invention, for treatment or prevention of diabetes or metabolic syndrome.

In one embodiment, the patient subjected to the treatment or prevention of diabetes or metabolic syndrome with the oral dosage forms according to the invention is a child, such as a human subject under the age of 18 years.

In one embodiment, the method of treatment or prevention according to the invention comprises administering to a patient in need thereof a daily GABA dose of 200-1200 mg/day, such as 200, 400, 600, 800, 1000 or 1200 mg/day.

In carrying out the present invention, the skilled person may rely on a number of text books providing common general knowledge in the art, such as e.g. Remington: The Science and Practice of Pharmacy, $21^{st}$ ed., ISBN 0-7817-4673-6, and Pharmacology, Brenner & Stevens, $3^{rd}$ ed. 2010 (Saunders, Philadelphia, USA), which are included herein by reference.

EXAMPLES

The invention is further illustrated by a number of examples. The examples shall not be construed as limiting the scope of the invention, which is that of the appended claims.

Production of Tablets

Five formulations of GABA with different release characteristics were produced and evaluated. Tablets were produced by direct compression and compacted to a 500 mg fill weight with a target hardness of 110 N. A 10 mm round concave tooling was used for the compression on a single punch F press.

Formulation 1

| Ingredient | Function | Composition (w/w %) | Mass per tablet (mg) |
| --- | --- | --- | --- |
| GABA | Active ingredient | 40 | 200 |
| Microcrystalline cellulose | Filler | 36.75 | 183.75 |
| Dicalcium phosphate | Filler | 16.75 | 83.75 |
| Croscarmellose sodium | Disintegrant | 5 | 25.00 |
| Silicon dioxide | Glidant | 0.5 | 2.5 |
| Magnesium stearate | Lubricant | 1 | 5 |
| Total | | 100 | 500 |

Formulation 2

| Ingredient | Function | Composition (w/w %) | Mass per tablet (mg) |
| --- | --- | --- | --- |
| GABA | Active ingredient | 40 | 200 |
| HPMCP Methocel™ E50LV | Filler | 30 | 150 |
| Microcrystalline cellulose | Filler | 28.5 | 142.5 |
| Silicon dioxide | Glidant | 0.5 | 2.5 |
| Magnesium stearate | Lubricant | 1 | 5 |
| Total | | 100 | 500 |

Formulation 2a

| Ingredient | Function | Composition (w/w %) | Mass per tablet (mg) |
| --- | --- | --- | --- |
| GABA | Active ingredient | 40 | 200 |
| HPMCP Methocel™ E50LV | Filler | 35 | 175 |
| Microcrystalline cellulose | Filler | 23.5 | 117.5 |
| Silicon dioxide | Glidant | 0.5 | 2.5 |
| Magnesium stearate | Lubricant | 1 | 5 |
| Total | | 100 | 500 |

Formulation 3

| Ingredient | Function | Composition (w/w %) | Mass per tablet (mg) |
| --- | --- | --- | --- |
| GABA | Active ingredient | 40 | 200 |
| HPMCP Methocel™ K100LV | Filler | 30 | 150 |
| Microcrystalline cellulose | Filler | 28.5 | 142.5 |
| Silicon dioxide | Glidant | 0.5 | 2.5 |
| Magnesium stearate | Lubricant | 1 | 5 |
| Total | | 100 | 500 |

Formulation 4

| Ingredient | Function | Composition (w/w %) | Mass per tablet (mg) |
| --- | --- | --- | --- |
| GABA | Active ingredient | 40 | 200 |
| HPMCP Methocel™ K4M | Filler | 30 | 150 |
| Microcrystalline cellulose | Filler | 28.5 | 142.5 |
| Silicon dioxide | Glidant | 0.5 | 2.5 |
| Magnesium stearate | Lubricant | 1 | 5 |
| Total | | 100 | 500 |

The formulations 2-4 were developed with an aim to target different release profiles. Two types of Methocel™ (HPMCP) were assessed, types K and E. Type K is known to form stronger gels than type E and is suitable for controlled release matrices targeting slower release rates. Along with the two types, various viscosities were assessed where Methocel™ grades with a higher viscosity form stronger gel barriers for diffusion resulting in slower drug release rates. Along with the rate controlling polymer, microcrystalline cellulose was also included in the tablets to give elasticity.

In formulations using grade E50 Methocel™, which forms a weaker gel, the percentage of HPMCP in the formulation could be increased to about 35%, as shown in Formulation 2b. This could be further combined with introduction of a less viscous grade of type E HPMCP, such as E3, E5, E6 or E15, while keeping the relative amount of HPMCP at 30-35% of the dosage form. Type K HPMCP grade K4M has a methoxyl substitution grade of 19-24% and a viscosity of 2,663-4,970 mPa·s 2% in water at 20° C. Type K HPMCP grade K100LV has a methoxyl substitution grade of 19-24% and a viscosity of 80-120 mPa-s 2% in water at 20° C.

Dissolution Rates

Dissolution rates using the tablets produced as described above were measured in an USP dissolution apparatus 2 in 1000 ml of 0.01M HCl where the tablets were mixed using a paddle speed of 50 rpm at 37° C.

Figure 1:
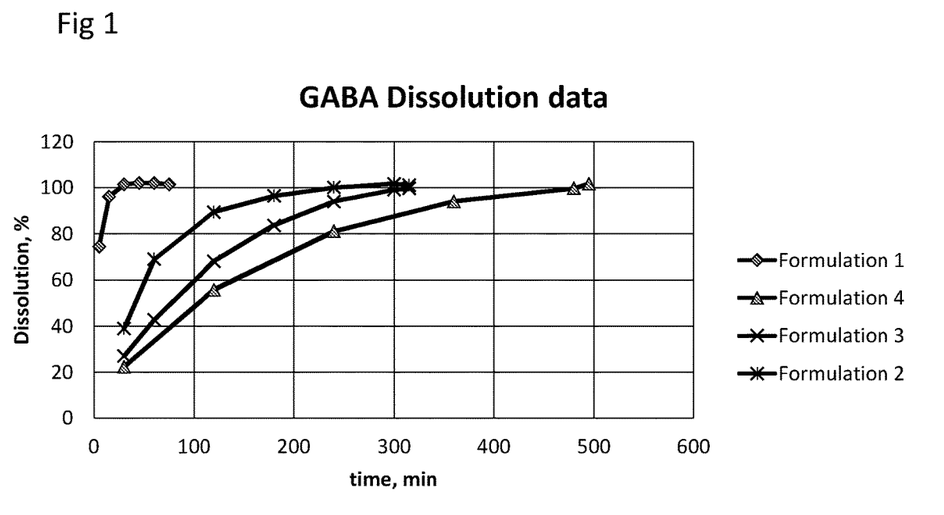
FIG. 1 shows dissolution data for a number of GABA formulations.

Dissolution rates for formulations 1, 2, 3, and 4 are shown in FIG. 1.

Pharmacokinetics

The pharmacokinetic profile of GABA in dogs following oral administration of the four formulations according to the above was evaluated.

Figure 2:
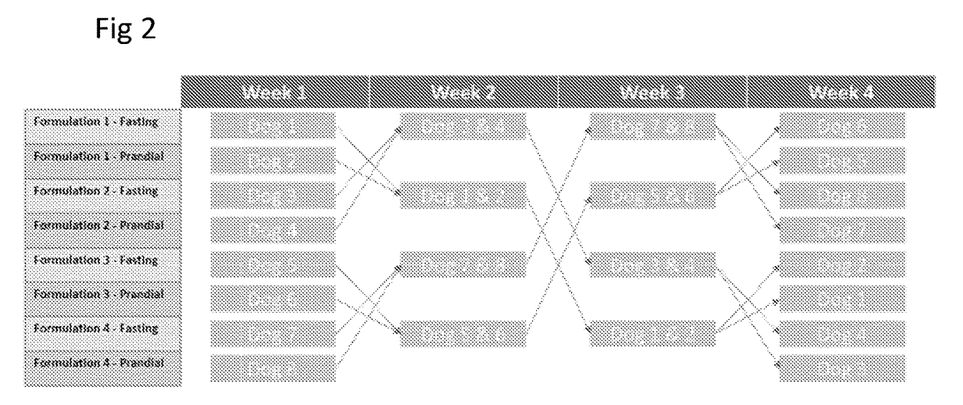
FIG. 2 is a study protocol for studying the pharmacokinetics for a number of GABA formulations.

8 male dogs of age 1-6 years were included in the study. The dogs were divided into four groups of two dogs each. A cross-over administration scheme for the formulations was designed, as shown in FIG. 2. The administered dose levels are provided in Table 1.

TABLE 1

| Dog weight kg | GABA 100 mg/kg | Total GABA mg | Number of 200 mg tablets |
|---|---|---|---|
| 8.5 | 100 | 850 | 4 |
| 10.5 | 100 | 1050 | 5 |
| 11.2 | 100 | 1120 | 6 |
| 11.9 | 100 | 1190 | 6 |
| 12.2 | 100 | 1220 | 6 |
| 13.2 | 100 | 1320 | 7 |
| 14.5 | 100 | 1450 | 7 |
| 15.7 | 100 | 1570 | 8 |

Study Schedule

Per each time-point per dog, the following aliquots of plasma was prepared:
K2EDTA tubes: 1 aliquot of 500 µl (for potential hematology analysis)
Lithium heparin tubes:
  1 aliquot of 200 µl (for potential GLP-1 analysis): Immediately (<30 seconds) after blood collection (≈500 µl blood), appropriate amount of DPP-IV inhibitor (Merck) was added according to manufacturer's instructions before plasma separation.
  5-7 aliquots of 200 µl for clinical biochemistry, GABA analysis and further other hormones/analyses.
Aliquots were shipped directly in dry ice to the bioanalytical test site or stored frozen until further analysis.

Aliquoting of urine samples (n=128) depending on the collected amount (0.5 mL per tube) and storage and/or shipment according to further analyses.

Plasma samples (n=320, all time-points) was analyzed for levels of GABA and pharmacokinetic (PK) parameters were calculated.

For each cycle, 5 plasma samples per animal (4, 5, 7, 10 and 24 h post administration) were analyzed for toxicity parameters as below (i.e. 40 samples per cycle, total of 160 samples).

Clinical biochemical parameters (reduced panel): Dosing of LDH, ALT, ALKP. Needed volume of plasma per sample: 200 µl in lithium heparin tube.

Insulin (ELISA): Needed volume of plasma per sample: 150-200 µl in lithium heparin tube.

Treatment

GABA was administered at t=0 via Per Os administration according to FIG. 2 and Table 1. The capsules were put directly into the digestive tract. For fasted dogs, GABA capsules were administered without food and for the non-fasted dogs, GABA capsules were administered with food (same amount of food given to all animals). The dogs were usually fed in the evening. For fasted dogs, food was given in the evening before the experiment. After the blood sample collection at 10 h, food was given to all dogs.

Blood Collection

For blood collection, a 5 ml syringe (TERUMO) was used and blood sampling was directly collected at the jugular vein. Blood samples were collected in K2-EDTA tubes and into Li-heparin tubes, at the following time points:
t=0 (baseline/blank), 0.5, 1, 2, 3, 4, 5, 7, 10 and 24 hours following administration (total of 80 samples per cycle).

For each group, blood was drawn from all 8 dogs.

Urine Collection

Total urine was collected via catheter at 4 time-points: at t=0 (baseline/blank), and then at 4 h, 8 h and 12 h following administration (total of 32 samples per cycle). Samples were stored frozen and/or shipped according to further analyses.

Blood Samples Preparation

Blood samples were centrifuged for 10 minutes at 1500 g at 4° C. for plasma separation. Plasma was be harvested by use of pipettes, transferred immediately to clean 1.5 ml Eppendorf tubes and stored in dry ice for shipment and in case of not immediate shipment the samples were stored in a freezer. Each vial was labelled with date, study code, dog number and group and time-point.

Analysis of Plasma Samples

Plasma samples were analyzed by LC/MS-MS for GABA levels. Also, some samples were analyzed for toxicology parameters and hormones: dosing of LDH, ALT and ALKP as well as insulin.

Results

The bioavailability of formulations 1, 2, 3, and 4 was evaluated in terms of plasma GABA concentrations over time, Area Under the plasma concentration Curve (AUC) for 5 h and 24 h after administration, respectively, peak plasma concentration (Cmax) and time for peak plasma concentration (Tmax).

Figure 3:
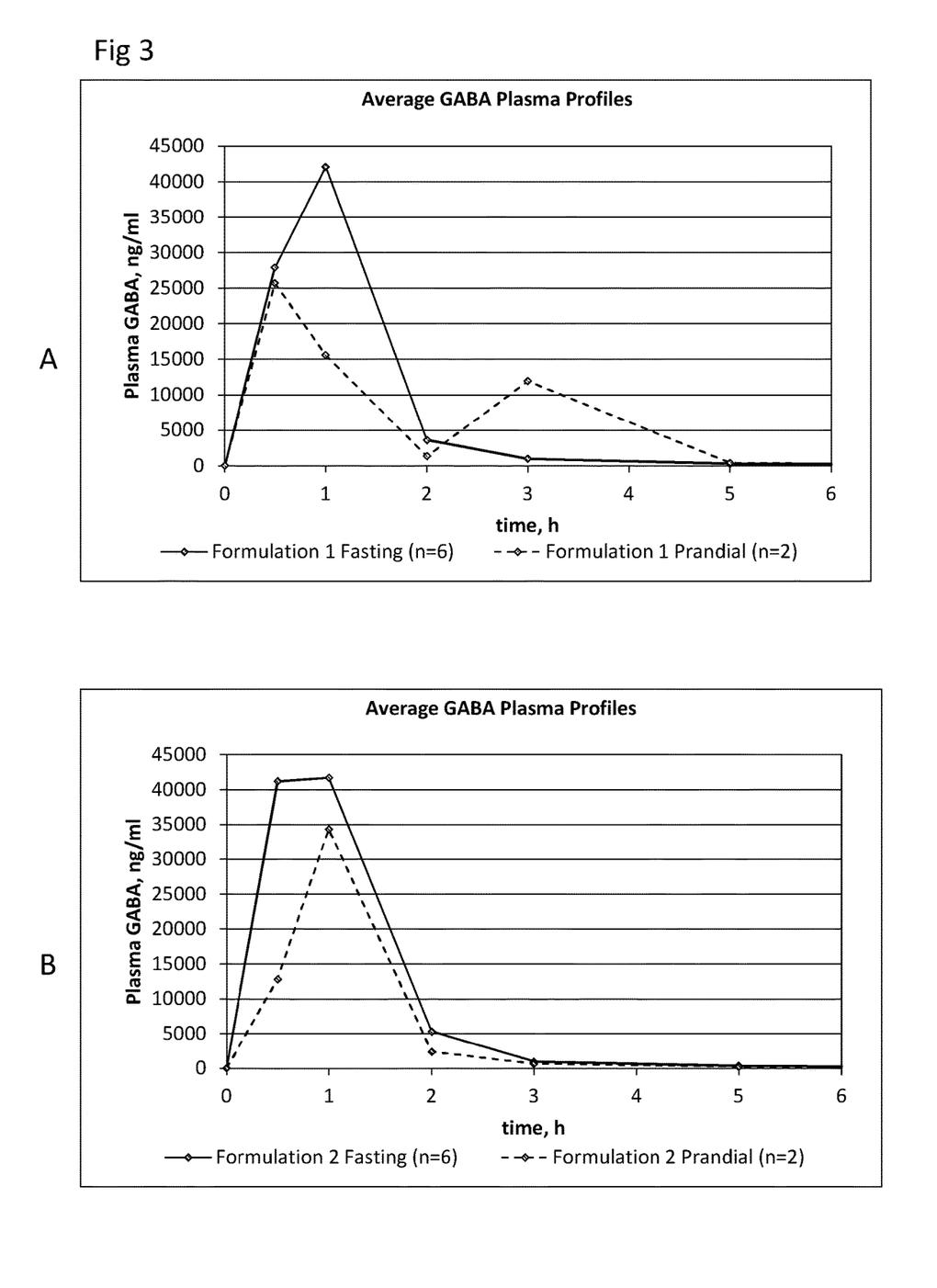
FIG. 3 shows GABA plasma concentration curves and dissolution data for the studied GABA formulations.

Plasma concentrations over time are shown in FIG. 3.

Figure 4:
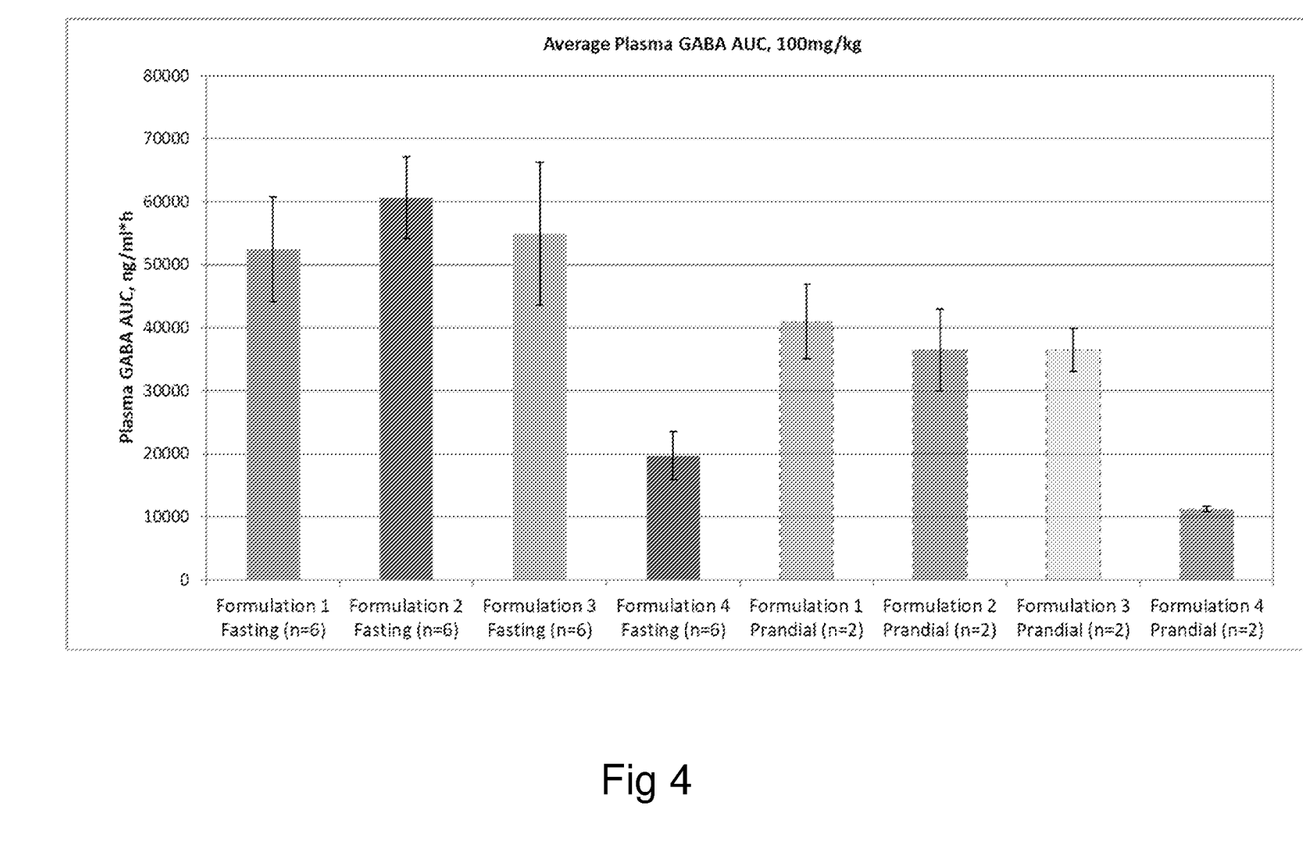
FIG. 4 shows the AUC for the studied GABA formulations.

The AUC (24 h) values are shown in table 2 and FIG. 4.

TABLE 2

| Formulation | Administration | AUC |
|---|---|---|
| 1 | Fasting | 52472 |
| 1 | Fed | 40986 |
| 2 | Fasting | 60691 |
| 2 | Fed | 36500 |
| 3 | Fasting | 54890 |
| 3 | Fed | 36478 |
| 4 | Fasting | 19684 |
| 4 | Fed | 11178 |

It was found that formulations 1, 2, and 3 have desirable bioavailability characteristics in that they provide high bioavailability in terms of AUC (24 h) and also can be taken both with and without food and formulation 1 provides comparable bioavailability of GABA irrespective of accompanying meals.

Comparison with Prior Art Formulations

A comparison was made with the results provided by Li and co-workers (Li et al., Frontiers in Pharmacology, (2015) 6:260) and a standard Over The Counter food supplement in the form of a powder (NOW Foods, Chicago, USA).

AUC (24 h) data were taken from Table 1 of Li et al.

Figure 5:
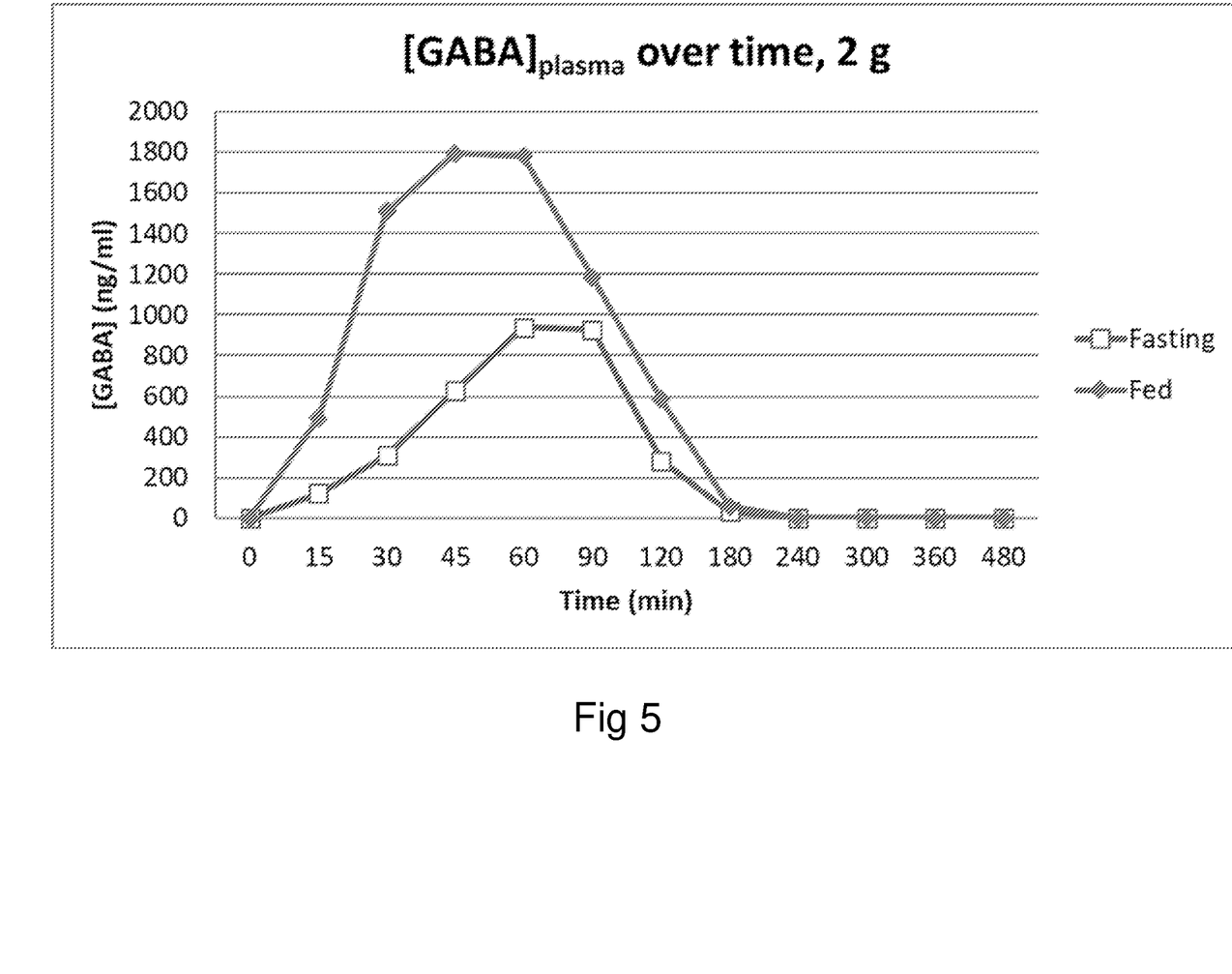
FIG. 5 shows average serum concentration of GABA over time for a prior art formulation.

Data for the food supplement product was obtained from a study on 4 healthy human individuals receiving 2 g GABA either with or without food. Serum blood draws were obtained at baseline (t=0) and at 15 min, 30 min, 45 min, 60 min, 90 min, 2 h, 3 h, 4 h, 5 h, 6 h. The average serum concentration of GABA over time is shown in FIG. 5.

The dose given to the human subjects in the food supplement study and Li et al. was 2 g to adults, which in the case of Li et al. weighed on average 62 kg. The dose was thus about 32 mg/kg. The dose in the dog study of the formulations of the present disclosure was about 100 mg/kg. This corresponds to a Human Equivalent Dose of 54 mg/kg (Nair A B, Jacob S. A simple practice guide for dose conversion between animals and human. J Basic Clin Pharma 2016; 7:27-31), i.e. about 1.7 times higher. To compare the bioavailability across species, the AUC(24 h) values for the new formulations tested in dogs were thus divided by 1.7.

Figure 6:
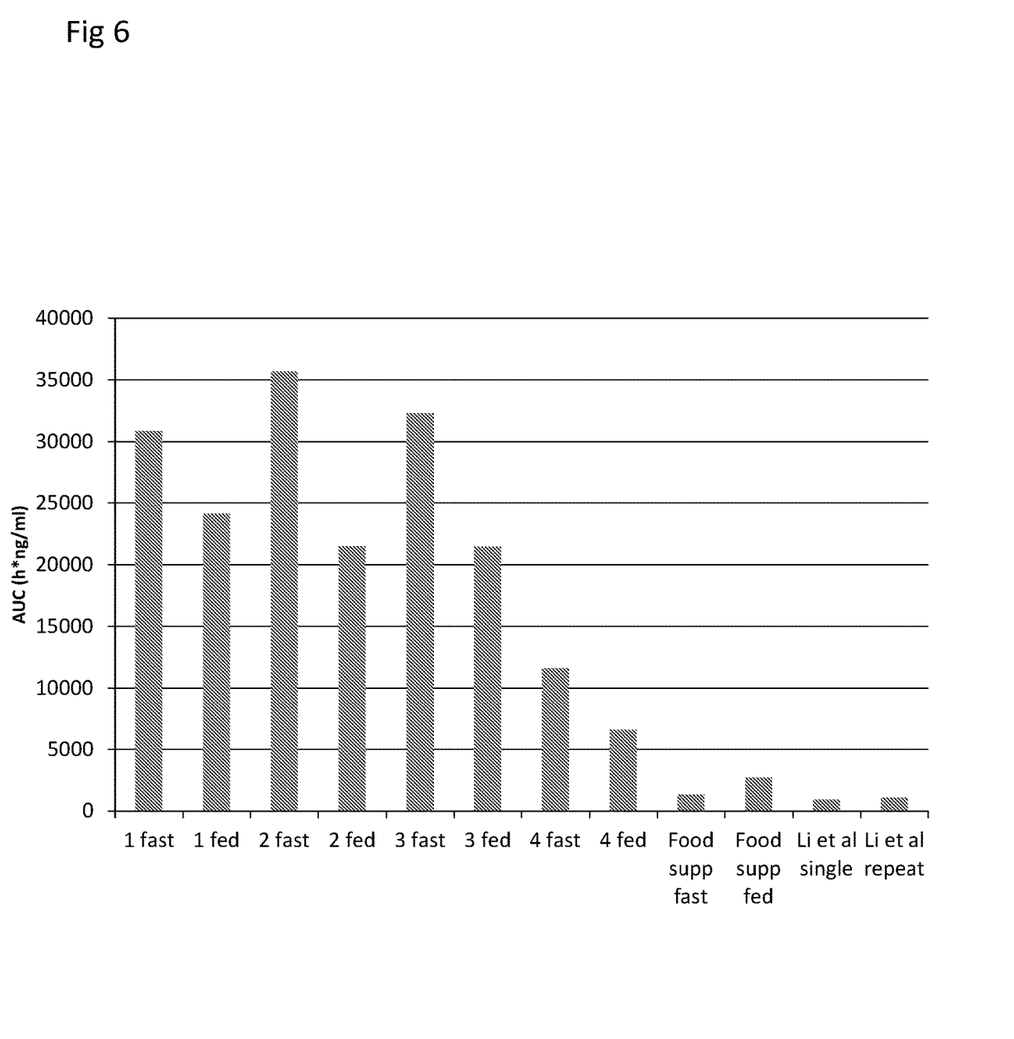
FIG. 6 shows the AUC for the studied GABA formulations and prior art formulations.

The AUC values are compared in Table 3 and FIG. 6

TABLE 3

| Formulation | Administration | AUC |
|---|---|---|
| 1 | Fasting | 30866 |
| 1 | Fed | 24109 |
| 2 | Fasting | 35701 |
| 2 | Fed | 21470 |
| 3 | Fasting | 32288 |
| 3 | Fed | 21458 |
| 4 | Fasting | 11579 |
| 4 | Fed | 6575 |
| Food supplement | Fasting | 1326 |
| Food supplement | Fed | 2711 |
| Li et al. | single dose | 933 |
| Li et al. | repeated dose | 1078 |

It is clear from the comparative data that the bioavailability of formulations 1, 2, and 3 are significantly improved over the existing formulations in terms of bioavailability as indicated by AUC (24 h), and also superior to formulation 4.

Study to Investigate the Effect of Oral GABA Therapy on β-Cell Regeneration in Type 1-Diabetes Patients The following protocol can be used to investigate the effect of oral GABA therapy on β-cell regeneration in type 1-diabetes patients, using the oral dosage forms of the present invention.

Objectives:

Primary Objective

The primary objective is to evaluate the acute and long-term safety of oral GABA treatment.

Secondary Objectives

The secondary objectives are to evaluate the differences in effect between the two treatment groups. As well as to analyze the outcome of oral GABA treatment on regaining endogenous insulin secretion as measured by C-peptide, overall diabetes status, safety of treatment, serum levels of GABA, effects on the immune system and quality of life (QoL) of the patients.

Study Design:

The first part of the study will include 6 patients and be performed as a Safety and Dose Escalation study in three steps, with a low (200 mg), medium (600 mg) and high dose (1200 mg) of GABA. Safety parameters, plasma concentration of GABA, insulin and glucose tolerance will then be evaluated. If no safety concerns are arisen the subjects already included in this part of the study will then be enrolled in the main study.

The main study is a 2-arm, open label, single center, clinical trial. Eligible patients will be randomized into one of two active treatment arms to receive oral GABA treatment for 6 months. Patients will be followed for a total of 7-8 months, depending on assigned treatment group. All patients will continue to receive their normal standard of care and intensive insulin treatment from their personal physicians during the whole study period.

Selection of Patients:

Patients should be ≥18 and ≤50 years old and they must have been diagnosed with type-1 diabetes (T1D) before the age of 25. Patients eligible for enrollment must have had their T1D diagnosis for ≥5 years and their fasting c-peptide levels should be in the range from undetectable levels up to <0.12 nmol/L. Exclusion criteria in the study are females of child-bearing potential, males not using effective contraception, ongoing breast feeding, eGFR<60 ml/min, known cancer disease, indications of liver disease with increased plasma concentrations of alanine or aspartate aminotransferases, previous history of pancreatitis or other exocrine pancreatic disorder, HbA1c>90 mmol/mol.

Number of Patients Planned: Approximately 24 patients will be enrolled. To ensure that 24 patients are enrolled approximately 35 patients will be screened.

Description of Treatment Groups:

Safety and Dose Escalation Study:

6 patients will be assessed for eligibility and will then be included in the safety evaluation and dose escalation part of the study. Patients will receive a low (200 mg), medium (600 mg) and high dose (1200 mg) of GABA to evaluate pharmacokinetics and safety. The safety of GABA treatment will be assessed by a Data Safety Monitoring Board (DSMB) and if no safety concerns are raised the main study will start.

Main Study:

Patients will be assessed for eligibility at the screening visit (Visit 1) 14 to 28 days prior to Visit 2 (Day 1) where patients eligible for the study will be randomized into 1 of 2 treatment groups.

Approximately 12 patients will be assigned to receive a low dose (200 mg) of GABA for 6 months. After 3 months, the safety of GABA treatment will be assessed by a DSMB. If no safety concerns are raised the treatment will continue for another 3 months and treatment arm 2 will start.

approximately 12 patients will be assigned to receive a high dose (600 mg) of oral GABA treatment between Month 1 and 7 (from Day 44 to Day 225). After 1 month, the safety of GABA treatment will be assessed by a DSMB. If no safety concerns are raised the treatment will continue for another 5 months.

Endpoints:

Primary Endpoint:

Number of AEs/SAEs possibly or probably related to GABA treatment

Changes in laboratory parameters, physical examinations and vital signs over time vs baseline values Secondary Endpoints:

Difference in C-peptide (Area Under the Curve [AUC] mean 0-120 min) during a Mixed Meal Tolerance Test (MMTT) between baseline and after 6 months of oral GABA treatment.

Difference in C-peptide (Area Under the Curve [AUC] mean 0-120 min) during a MMTT between baseline and after 3 and 6 months of treatment and between baseline and the follow-up visit.

Difference in C-peptide (Area Under the Curve [AUC] mean 0-120 min) during a MMTT between baseline and after 3 and 6 months of treatment and between baseline and the follow-up visit. Analyzed with an ultra-sensitive ELISA.

Difference in maximum stimulated C-peptide during a MMTT between baseline and after 3 and 6 months of treatment and between baseline and the follow-up visit.

Difference in maximum stimulated C-peptide during a MMTT between baseline and after 3 and 6 months of treatment and between baseline and the follow-up visit. Analyzed with an ultra-sensitive ELISA.

Difference in C-peptide (Area Under the Curve [AUC] mean 0-120 min) during a MMTT between treatment group 1 and 2 after 3 and 6 months of treatment and between baseline and the follow-up visit.

Difference in glucagon (Area Under the Curve [AUC] mean 0-120 min) during an Hypoglycemic Clamp between baseline and 6 months of treatment.

Difference in glucagon (Area Under the Curve [AUC] mean 0-120 min) during an Hypoglycemic clamp between treatment group 1 and 2 between baseline and 6 months of treatment.

Variables that indicate diabetes status such as plasma C-peptide, glucagon, glucagon like-peptide 1, lipids and Hemoglobin A1c (HbA1c). Daily exogenous insulin consumption, variability of blood sugar, and number of self-reported hypoglycemia.

Variables that indicate effects on the immune system such as serum autoantibodies (and isotypes) to GAD65 and Islet Antigen-2 and a general profiling of the immune cells in the blood.

Analysis of GABA plasma levels after 3 and 6 months of treatment and at the follow-up visit.

Measurement of patient QoL by the DTSQ questionnaire.

Measurements of patient QoL by the RAND-36 questionnaire.

Sample Size:

The main secondary endpoint that will be used to assess efficacy potential will be the proportion of C-peptide values from a 2-hour MMTT that show improvement from baseline after treatment. Our approach maximizes the number of data points available for analysis and is based on the observation that each 120-minute MMTT yields 6 measurements of C-peptide (at times 0, 15, 30, 60, 90, 120 minutes). A total sample size of 20 subjects is thus planned to ensure 80% power to detect a benefit rate of 1.5%

Analysis of Secondary Endpoint Variables:

Delta-change in C-peptide (Area Under the Curve $[AUC]_{mean\ 0\text{-}120\ min}$) between MMTTs will be analyzed by paired two-sided Student's t test. Repeated measurements ANOVA will be applied to evaluate change in other parameters during course of the study. Analysis of the QoL data obtained within the study will be assessed with the RAND-36 and diabetes treatment satisfaction questionnaire (DTSQ).

Trial Design

Description of the Study Design and Procedures

Patients will provide written informed consent before any study-related procedures are performed. The first part of the study will include 6 patients and be performed as a Safety and Dose Escalation study in three steps, with a low (200 mg), medium (600 mg) and high dose (1200 mg) of GABA. Safety parameters, plasma concentration of GABA, insulin and glucose tolerance will then be evaluated. After the first patient has completed the three doses escalation steps a DSMB will review the safety data and if no safety concerns are arisen the other 5 patients will be allowed to start.

The treatment schedule is given in the table below.

When all 6 patients have completed the dose-escalation study a DSMB will again review the safety data. If no safety concerns are arisen the subjects already included in this part of the study will then be enrolled in the main study, after a washout period of at least 1 month.

The main study is a 2-arm, open label, single center, clinical trial. Eligible patients will be randomized into one of two active treatment arms to receive oral GABA treatment for 6 months. Patients will be followed for a total of 7-9 months, depending on assigned treatment group. All patients will continue to receive their normal standard of care and intensive insulin treatment from their personal physicians during the whole study period.

On Day 1 (Visit 2), 2-4 weeks after the Screening Visit (the patients that were included in the dose-escalation study will not do a screening visit but will have a washout period of at least 1 month), patients eligible for the study will be randomized in a 1:1 ratio stratified by the C-peptide level to receive:

1) 200 mg of GABA for 6 months (from Day 1 to Day 181),
or
2) 600 mg of GABA for 6 months (from Day 44 to Day 225)

The treatment schedule for Arm 1 and Arm 2 is described in the tables below.

At the screening visit patients will be assigned a 3-digit sequential screening number, which will be used as a 3-digit patient identification (Patient Number), i.e. XXX.

Individual patients will be exposed to GABA for 6 months. All patients will continue to receive intensive insulin treatment from their personal physicians during the whole study period.

Schedule of Patient Visits for Safety and Dose Escalation Study Period:

| | Screening Day −14 to −28 | Baseline | | Intervention | | | | | | |
|---|---|---|---|---|---|---|---|---|---|---|
| Visit no: | Screening 1 | Day 1 2 | Day 2 3 | Day 3 4 | Day 5 5 | Day 6 6 | Day 8 7 | Day 9 8 | Day 10 9 | Day 11* 10 |
| 6subjects | | MMTT Baseline samples | Hypoglycemic clamp | Treatment start, PK curve | Safety, Hypoglycemic clamp | Dose escalation, Safety, PK curve | Safety, Hypoglycemic clamp | Dose escalation, Safety, PK curve | Safety, Hypoglycemic clamp | Safety, MMTT |
| Dose/day | | | | 200 mg of GABA | | 600 mg GABA | | 1200 mg of GABA | | |

*A DSMB will evaluate the first patient and decide if the other 5 patients can enter the study. After all 6 patients have completed the dose escalation steps the DSMB will again review the safety data and decide if the main study can start Schedule of Patient Visits for Main Study Period—Arm 1

| | GABA Study | | | | | | | | | |
|---|---|---|---|---|---|---|---|---|---|---|
| | | Intervention | | | | | | | | |
| | Screening Day −14 to −28 Screening | Day 1 and 2 BASELINE VISIT & Randomization | Day 7 | Day 30* | Day 90 M3 | Day 180 and 181 M6 | | Follow-up Day 210 M7 | Follow-up Day 211 M7 | |
| Visit no: | 1 | 2 | 3 | 4 | 5 | 6 | 7 | 8 | 9 | 10 |
| Group 1 (12 subjects) | | MMTT, Baseline samples | Hypogly-cemic Clamp | Safety | | MMTT, Safety | MMTT, Safety | Hypogly-cemic clamp | MMTT | Hypogly-cemic clamp |
| Dose/day | | | | Low dose of GABA (200 mg/day) | | | | | | |

Schedule of Patient Visits for Main Study Period—Arm 2

| | GABA Study | | | | | | | | | | |
|---|---|---|---|---|---|---|---|---|---|---|---|
| | | Intervention | | | | | | | | | |
| | Screening Day −14 to −28 Screening | Day 1 and 2 BASELINE VISIT & Randomization | Day 44 Month 2* | Day 51 M2 | Day 74 M3# | Day 134 M5 | Day 224 and 225 M8 | | Follow-up Day 254 M9 | Follow-up Day 255 M9 | |
| Visit no: | 1 | 2 | 3 | 4 | 5 | 6 | 7 | 8 | 9 | 10 | 11 |
| Group 2 (12 subjects) | | MMTT, Baseline samples | Hypogly-cemic clamp | Treatment start, MMTT | | Safety | MMTT, Safety | MMTT, Safety | Hypogly-cemic clamp | MMTT | Hypogly-cemic clamp |
| Dose/day | | | | | High dose of GABA (600 mg/day) | | | | | | |

*DSMB will evaluate the safety data of the first 4 patients included and decide if the second treatment arm can start. Therefore, start of treatment for treatment arm 2 will be delayed.
The DSMB will evaluate the safety data of the first 4 patients included in treatment arm 2 after 1 month of treatment to make sure that no safety concerns have arisen upon treatment with the higher dose of GABA.

Schedule of Events for Safety and Dose Escalation Study

| | Event | | | | | | | | | |
|---|---|---|---|---|---|---|---|---|---|---|
| DAY | V1 Screening −14 to −28 | V2 Baseline Visit 1 | V3 Baseline Visit 2 | V4 3 | V5 5 | V6 6 | V7 8 | V8 9 | V9 10 | V10 11 |
| Informed Consent | X | | | | | | | | | |
| Eligibility check | X | X | | | | | | | | |
| Demographics | X | | | | | | | | | |
| Medical History | X | | | | | | | | | |
| Family history of T1D | X | | | | | | | | | |
| GABA start/end | | | | X | | | | | X | |
| Dose escalation | | | | | | X | X | | | |
| General Physical Exam | X | X | | | | X | X | X | | |
| Neurological Assessment | X | X | | | | X | X | X | | |
| ECG | X | X | | | | X | X | X | | |
| Concomitant Medication | X | X | | | | | | | | |
| Vital signs (BP) | X | X | | | | X | X | X | | |
| AEs | | | | | X | X | X | X | X | X |
| Self-reported severe hypoglycemia | | X | | | | X | X | | X | |
| MMTT | | X | | | | | | | | X |

-continued

|  | Event | | | | | | | | | |
|---|---|---|---|---|---|---|---|---|---|---|
| DAY | V1 Screening −14 to −28 | V2 Baseline Visit 1 | V3 Baseline Visit 2 | V4 3 | V5 5 | V6 6 | V7 8 | V8 9 | V9 10 | V10 11 |
| Hypoglycemic clamp | | | X | | X | | X | | X | |
| FreeStyle LibrePro, FGM, start/end | X | X | | | | | | | | X |
| *Blood Sampling for Safety, GABA levels and Immunology:* | | | | | | | | | | |
| Hematology | X | X | | | X | | X | | | X |
| Clinical Chemistry | X | X | | | X | | X | | | X |
| GABA level | | X | | | | | | | | X |
| GABA PK Curve | | | | X | | X | | X | | |
| Immunological parameters | | X | | | | | | | | X |
| *Urine Analysis:* | | | | | | | | | | |
| Micro-albuminuria | X | X | | | X | X | X | X | | X |
| Creatinine | X | X | | | X | X | X | X | | X |
| GABA | | X | | X | | X | X | | | |
| *Blood Sampling for Diabetes Status:* | | | | | | | | | | |
| Fasting C-peptide | X | X | | | | | | | | X |
| MMTT-induced C-peptide | | X | | | | | | | | X |
| HbA1c | X | X | | | | | | | | |
| Fasting Glucose | X | X | | | X | X | X | X | | X |
| MMTT-induced Glucose | | X | | | | | | | | X |
| Clamp-induced glucagon, epinephrine, norepinephrine, growth hormone and cortisol | | | X | | X | | X | | X | |
| Clamp-induced Glucose | | | X | | X | | X | | X | |

Abbreviations:
AEs = Adverse Events;
BP = Blood Pressure;
HBA1c = Hemoglobin A1c;
MMTT = mixed meal tolerance test;
ITT = Insulin Tolerance Test;
FGM = Flash Glucose Monitoring;
T1D = Type 1 Diabetes;
PK = Pharmacokinetic Schedule of Events for Main Study Period—Treatment Arm 1

|  | Event | | | | | | | | | |
|---|---|---|---|---|---|---|---|---|---|---|
| DAY | V1 Screening −14 to −28 | V2 Baseline Visit 1 | V3 Baseline Visit 2 | V4 Month 1 7 (±3) | V5 Month 1 30 (±5) | V6 Month 3 90 (±5) | V7 Month 6 180 (±5) | V8 Month 6 181 (±5) | V9 Month 7 210 (±14) | V10 Month 7 211 (±14) |
| Informed Consent | X | | | | | | | | | |
| Eligibility check | X | X | | | | | | | | |
| Demographics | X | | | | | | | | | |
| Randomization | | | X | | | | | | | |

-continued

| DAY | V1 Screening −14 to −28 | V2 Baseline Visit 1 | V3 Baseline Visit 2 | V4 Month 1 7 (±3) | V5 Month 1 30 (±5) | V6 Month 3 90 (±5) | V7 Month 6 180 (±5) | V8 Month 6 181 (±5) | V9 Month 7 210 (±14) | V10 Month 7 211 (±14) |
|---|---|---|---|---|---|---|---|---|---|---|
| Medical History | X | | | | | | | | | |
| Family history of T1D | X | | | | | | | | | |
| GABA start/end | | | X | | | | | X | | |
| General Physical Exam | X | X | | X | X | X | X | | X | |
| Neurological Assessment | X | X | | X | X | X | X | | X | |
| ECG | X | | | | X | | | | X | |
| Concomitant Medication | X | X | | X | X | X | X | | X | |
| Vital signs (BP) | X | X | | X | X | X | X | | | |
| Blood glucose and Insulin dose diary collected | | X | | X | X | X | X | | X | |
| Freestyle LibrePro, FGM | X | | | | | X | X | | X | |
| AEs | | | | X | X | X | X | X | X | |
| Self-reported severe hypoglycemia | | X | | X | X | X | X | X | X | |
| QoL questionnaire | | X | | | | | X | | X | |
| MMTT | | X | | | | X | X | | X | |
| Hypoglycemic Clamp | | | X | | | | | X | | X |
| Stool samples | | X | | | | X | X | | X | |
| Hand out patient blood glucose and insulin diary | X | X | | X | X | X | X | | | |
| Blood Sampling for Safety, GABA levels and Immunology: | | | | | | | | | | |
| Hematology | X | X | | X | X | X | X | | X | |
| Clinical Chemistry | X | X | | X | X | X | X | | X | |
| GABA level | | X | | X | X | X | X | | X | |
| PBMC and/or Immunological parameters | | X | | | X | X | X | | X | |
| Urine Analysis: | | | | | | | | | | |
| Micro-albuminuria | X | X | | X | X | X | X | | X | |
| Creatinine | X | X | | X | X | X | X | | X | |
| Blood Sampling for Diabetes Status: | | | | | | | | | | |
| Fasting C-peptide | X | X | | | X | X | X | | X | |
| MMTT-induced C-peptide | | X | | | | X | X | | X | |
| HbA1c | X | X | | | X | X | X | | X | |
| Fasting Glucose | X | X | | X | X | X | X | | X | |
| MMTT-induced Glucose | | X | | | | X | X | | X | |
| Clamp-induced glucagon, epinephrine, norepinephrine, growth hormone and cortisol | | | X | | | | | X | | X |

-continued

|  | Event | | | | | | | | | |
|---|---|---|---|---|---|---|---|---|---|---|
| DAY | V1<br>Screening<br>−14 to −28 | V2<br>Baseline<br>Visit<br>1 | V3<br>Baseline<br>Visit<br>2 | V4<br>Month 1<br>7 (±3) | V5<br>Month 1<br>30 (±5) | V6<br>Month 3<br>90 (±5) | V7<br>Month 6<br>180 (±5) | V8<br>Month 6<br>181 (±5) | V9<br>Month 7<br>210 (±14) | V10<br>Month 7<br>211 (±14) |
| Clamp-induced Glucose |  |  | X |  |  |  |  | X |  | X |
| Glucagon, GLP-1, lipids |  | X |  |  | X | X | X |  | X |  |

Abbreviations:
AEs = Adverse Events;
BP = Blood Pressure;
HBA1c = Hemoglobin A1c;
MMTT = mixed meal tolerance test;
ITT = Insulin Tolerance Test;
FGM = Flash Glucose Monitoring;
T1D = Type 1 Diabetes;
QoL = Quality of Life;
PK = Pharmacokinetic Schedule of Events for Main Study Period—Treatment Arm 2

|  | Event | | | | | | | | | | |
|---|---|---|---|---|---|---|---|---|---|---|---|
| DAY | V1<br>Screening<br>−14 to −28 | V2<br>Baseline<br>1 | V3<br>Baseline<br>2 | V4<br>Month 2<br>44 (±3) | V5<br>Month 2<br>51 (±5) | V6<br>Month 3<br>74 (±5) | V7<br>Month 5<br>134 (±5) | V8<br>Month 8<br>224 (±5) | V9<br>Month 8<br>225 (±5) | V10<br>Month 9<br>254 (±14) | V11<br>Month 9<br>255 (±14) |
| Informed Consent | X |  |  |  |  |  |  |  |  |  |  |
| Eligibility check | X | X |  |  |  |  |  |  |  |  |  |
| Demographics | X |  |  |  |  |  |  |  |  |  |  |
| Randomization |  | X |  |  |  |  |  |  |  |  |  |
| Medical History | X |  |  |  |  |  |  |  |  |  |  |
| Family history of T1D | X |  |  |  |  |  |  |  |  |  |  |
| GABA start/end |  |  |  |  | X |  |  |  | X |  |  |
| General Physical Exam | X | X |  | X | X | X | X | X |  | X |  |
| Neurological Assessment | X | X |  | X | X | X | X | X |  | X |  |
| ECG | X |  |  |  |  | X |  |  |  | X |  |
| Concomitant Medication | X | X |  | X | X | X | X | X |  | X |  |
| Vital signs (BP) | X | X |  | X | X | X | X | X |  |  |  |
| Blood glucose and insulin dose diary collected |  | X |  | X | X | X | X | X |  | X |  |
| Freestyle LibrePro, FGM | X |  |  |  |  |  |  | X | X |  | X |
| AEs |  |  |  |  | X | X | X | X |  | X |  |
| Self-reported severe hypoglycemia |  | X |  | X | X | X | X | X |  | X |  |
| QoL questionnaire |  | X |  | X |  |  |  | X |  | X |  |
| MMTT |  | X |  | X |  |  | X | X |  | X |  |
| Hypoglycemic Clamp |  |  | X |  |  |  |  |  | X |  | X |
| Stool samples |  | X |  | X |  |  | X | X |  | X |  |

-continued

| DAY | V1 Screening −14 to −28 | V2 Baseline 1 | V3 Baseline 2 | V4 Month 2 44 (±3) | V5 Month 2 51 (±5) | V6 Month 3 74 (±5) | V7 Month 5 134 (±5) | V8 Month 8 224 (±5) | V9 Month 8 225 (±5) | V10 Month 9 254 (±14) | V11 Month 9 255 (±14) |
|---|---|---|---|---|---|---|---|---|---|---|---|
| Hand out patient blood glucose and insulin diary | X | X | | X | X | X | X | X | | | |
| Blood Sampling for Safety, GABA levels and Immunology: | | | | | | | | | | | |
| Hematology | X | X | | X | X | X | X | X | | X | |
| Clinical Chemistry | X | X | | X | X | X | X | X | | X | |
| GABA level | | X | | X | X | X | X | X | | X | |
| PBMC and/or Immunological parameters | | X | | | | X | X | X | | X | |
| Urine Analysis: | | | | | | | | | | | |
| Micro-albuminuria | X | X | | X | X | X | X | X | | X | |
| Creatinine | X | X | | X | X | X | X | X | | X | |
| Blood Sampling for Diabetes Status: | | | | | | | | | | | |
| Fasting C-peptide | X | X | | X | | X | X | X | | X | |
| MMTT-induced C-peptide | | X | | X | | | X | X | | X | |
| HbA1c | X | X | | X | | X | X | X | | X | |
| Fasting Glucose | X | X | | X | X | X | X | X | | X | |
| MMTT-induced Glucose | | X | | X | | | X | X | | X | |
| Clamp-induced glucagon epinephrine, norepinephrine, growth hormone and cortisol | | | X | | | | | | X | | X |
| Clamp-induced Glucose | | | X | | | | | | X | | X |
| Glucagon, GLP-1, lipids | | X | | X | | X | X | X | | X | |

Abbreviations:
AEs = Adverse Events;
BP = Blood Pressure;
HBA1c = Hemoglobin A1c;
MMTT = mixed meal tolerance test;
ITT = Insulin Tolerance Test;
FGM = Flash Glucose Monitoring;
T1D = Type 1 Diabetes;
QoL = Quality of Life;
PK = Pharmacokinetic

The invention claimed is:

1. An oral dosage form comprising gamma-aminobutyric acid (GABA), wherein the dosage form comprises 30-50% GABA 30-40% microcrystalline cellulose and 15-20% dicalcium phosphate, a disintegrant, and optionally pharmaceutically acceptable excipients.

2. The oral dosage form according to claim 1, wherein 100% of the GABA is released within 0.25-5 hours in 0.01 M HCl at 37° C. in a USP dissolution apparatus 2.

3. The oral dosage form according to claim 1, wherein at least 95% of the GABA is released after 4 hours in 0.01 M HCl at 37° C. in a USP dissolution apparatus 2.

4. The oral dosage form according to claim 1, wherein the dosage form exhibits a AUC (5h) when administered to a patient in fed state that is +/−30% as compared to AUC (5h) when administered to a patient in fasting state.

5. The oral dosage form according to claim 1, comprising 40% GABA.

6. A method for treatment of diabetes or metabolic syndrome in a subject comprising administering an oral dosage form according to claim 1 to said subject.

7. The method according to claim 6, wherein the subject is a human under the age of 18 years.

8. The method according to claim 7, comprising administering GABA in a dose of 200-1200 mg/day, such as 200, 600, or 1200 mg/day.

9. The oral dosage form according to claim 1, wherein the disintegrant is croscarmellose.

10. The oral dosage form according to claim 1, comprising 5% croscarmellose sodium.

11. The oral dosage form according to claim 1, comprising 30-50% GABA, 30-40% microcrystalline cellulose, 15-20% dicalcium phosphate, and 5% croscarmellose sodium.

12. The oral dosage form according to claim 1, comprising 40% GABA, 36.75% microcrystalline cellulose, 16.75% dicalcium phosphate, and 5% croscarmellose sodium.

13. The oral dosage form according to claim 12, wherein 100% of the GABA is released within 0.25-5 hours in 0.01 M HCl at 37° C. in a USP dissolution apparatus 2.

14. The oral dosage form according to claim 12, wherein at least 95% of the GABA is released after 4 hours in 0.01 M HCl at 37° C. in a USP dissolution apparatus 2.

15. The oral dosage form according to claim 12, wherein the dosage form exhibits a AUC (5h) when administered to a patient in fed state that is +/−30% as compared to AUC (5h) when administered to a patient in fasting state.

* * * * *